United States Patent [19]

Baldazzi et al.

[11] Patent Number: 5,446,152
[45] Date of Patent: Aug. 29, 1995

[54] HETEROCYCLIC COMPOUNDS ACTIVE IN GASTRO-INTESTINAL PATHOLOGIES

[75] Inventors: Claudia Baldazzi; Silvano Piani; Maria Barbanti; Egidio Marchi, all of Bologna, Italy

[73] Assignee: Alfa Wassermann S.p.A., Alanno, Italy

[21] Appl. No.: 223,697

[22] Filed: Apr. 6, 1994

[30] Foreign Application Priority Data

Apr. 16, 1993 [IT] Italy ................................ BO93A0155

[51] Int. Cl.$^6$ ............................................ C07D 413/06
[52] U.S. Cl. ........................... 544/123; 544/284; 544/287
[58] Field of Search ..................... 544/123, 284, 287

[56] References Cited

U.S. PATENT DOCUMENTS 3,177,252 4/1965 Thominet .
5,384,318 1/1995 Eggler et al. .

*Primary Examiner*—James H. Reamer
*Assistant Examiner*—John Peabody
*Attorney, Agent, or Firm*—Bucknam and Archer

[57] ABSTRACT

This invention refers to heterocyclic compounds of general formula

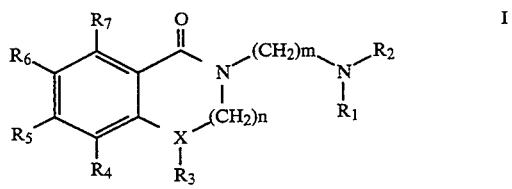

and their pharmacologically accepted salts.

The derivatives described in this invention are active in the gastro-intestinal apparatus; in particular, they have prokinetic effects, in other words they create specific stimulation on gastro-intestinal motility, facilitating the passage of the contents of the alimentary tract, and possess anti-emetic qualities, without side effects involving the central nervous system.

12 Claims, No Drawings

HETEROCYCLIC COMPOUNDS ACTIVE IN GASTRO-INTESTINAL PATHOLOGIES

SCOPE OF THE INVENTION

This invention refers to the synthesis of heterocyclic derivatives having favourable effects on gastro-intestinal motility, with prokinetic and anti-emetic properties and without side effects involving the central nervous system.

The principal derivatives with prokinetic properties used in therapy belong to the benzamide chemical class and their parent is metoclopramide, of the formula

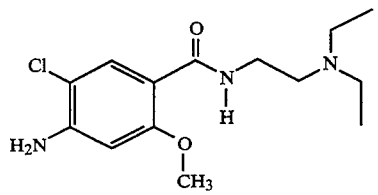

described in the U.S. Pat. No. 3,177,252, which stimulates the motility of the upper gastro-intestinal tract with a mechanism which probably implies interaction with receptors $5HT_4$, as reported by Brunnengräber R. et al., Pharma. Zeitung, 35, 9–18, 1991 and by Turconi M. et al., Drugs of the Future, 16, 1011, 1991, and has both central and peripheral antagonistic activity on the dopaminergic receptors $D_2$, as reported by King F. D. and Senger G. J., Ann. Rep. Med. Chem. 23, 201, 1990.

Over the last few years a large number of derivatives of metoclopramide, presenting structural modifications in the lateral chain, have been studied with the aim of leaving the prokinetic activity unaltered, though eliminating antagonism to the dopaminergic receptors. The antagonist action on these receptors, considered secondary in disorders of gastro-intestinal motility, seems to be of particular importance due to a series of undesirable side effects caused by drugs in use, such as extrapyramidal motor symptoms and high levels of prolactin in the blood.

The product currently used in therapy which best fulfils these pharmacological requirements is cisapride, with the formula

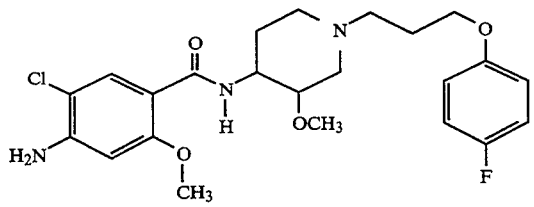

whose synthesis and pharmacological properties are described in the patent EP 0076530 and in Drugs of the Future, 13, 676, 1988.

Craig and Clarke, Brit. J. Pharm., 102, 563–564, 1991, report that cisapride stimulates intestinal motility through interaction with serotoninergic receptors $5HT_4$ and has practically no antagonist property of the dopamine receptors, of cholinesterase inhibition or direct parasympathomimetic activity.

King F. D. and Senger G. J., Ann. Rep. Med. Chem. 23, 202, 1990, report the structures of several other derivatives, structurally modified in lateral chain with respect to metoclopramide, and having prokinetic activity such as BRL 20627, dazopride, clebopride, which, unlike cisapride, show a fair amount of activity on the dopaminergic receptors $D_2$.

It is also known from the state of the art that some derivatives similar to those mentioned have a receptorial selectivity on the receptors $5HT_3$ with effects on the central nervous system such that they may also be used in the therapy of disturbances at a central nervous level.

This invention refers to new heterocyclic derivatives with a structure linked to the benzamide structure, substituted in position 2 of the aromatic ring with hydroxy or amino groups, for cyclization between the amide nitrogen atom and the amino or hydroxy radical in position 2 of the aromatic ring, designed according to evaluations of structure-activity on the products already described in the state of the art. The introduced structural variations influence the pharmacological properties of the derivatives, increasing their effect on gastro-intestinal motility and eliminating antagonism with the dopaminergic receptors, with the subsequent elimination of the undesirable effects on the central nervous system and on the endocrine constellation.

The derivatives described in this invention may be gainfully used in the treatment of a number of different pathologies of the gastro-intestinal tract such as nausea and vomit, also subsequent to anti-tumour treatments; gastro-esophageal regurgitation disease; functional dyspepsia from slowed gastric dumping; gastric hypomotility associated with anorexia nervosa; slowed gastric dumping and slowed intestinal transit during treatment with opiate analgesics (or in the case of opium-based drug dependence); gastroparesis of different origins (diabetic neuropathy); delayed gastric dumping; disturbances of gastro-duodenal motor coordination and functional disturbances of the upper alimentary tract in general; further applications at pediatric level may be as part of the treatment of disease from gastro-esophageal regurgitation, of pylorospasm or generally in slowed gastric dumping, regurgitations from cardial incontinence and cystic fibrosis.

DESCRIPTION OF THE INVENTION

This invention refers to new derivatives with a heterocyclic structure, to their pharmacologically acceptable salts and their therapeutic use in gastro-intestinal pathologies, as stimulators of gastro-intestinal motility, in other words as prokinetics and as antiemetics.

The compounds described in the claims of this invention have the following general formula:

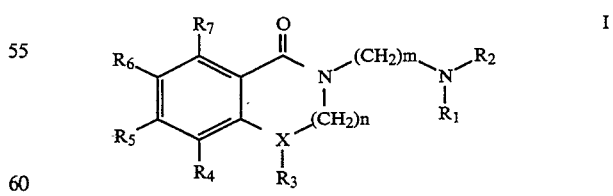

where X represents an atom of nitrogen or oxygen, n represents a whole number selected from 1 and 2, m a whole number between 1 and 4, $R_1$ and $R_2$, independently, represent an atom of hydrogen or a ($C_1$–$C_6$)-alkyl radical, with a linear or ramified chain, or $R_1$ and $R_2$ together with the nitrogen atom form a heterocyclic ting. $R_3$ represents null when X represents an atom of oxygen and it represents a hydrogen atom or a ($C_1$–$C_{10}$)-alkyl radical, with linear, ramified or cyclic chain, or a benzyl radical, when X represents a nitrogen atom. $R_4$, $R_5$, $R_6$ and $R_7$, independently, represent a hydrogen atom or a ($C_1$–$C_6$)-alkyl radical, with linear or ramified chain, or an atom of halogen. The compounds preferred in carrying out this invention are those in which $R_1$ and $R_2$, independently, represent a ($C_1$–$C_3$)-alkyl radical or a hydrogen atom or taken together with the nitrogen atom form a heterocyclic ring, $R_4$, $R_5$ and $R_7$ represent an atom of hydrogen, $R_6$ represents an atom of halogen, preferably an atom of chlorine, m is a whole number chosen between 2 and 3 and n corresponds to 1.

The derivatives of general formula I in which X represents an atom of nitrogen and n corresponds to 1 are obtained by means of a process which starts with the synthesis of benzamides of the general formula

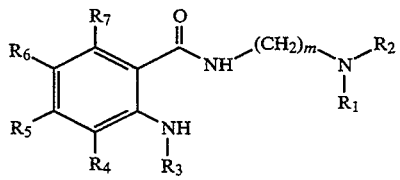  II in which $R_1$, $R_2$, $R_3$, $R_4$, $R_5$, $R_6$, $R_7$ and m have the above-mentioned meanings.

An isatoic anhydride of general formula

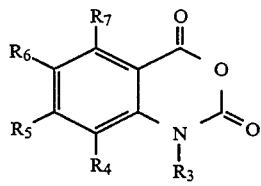  III is made to react with 1 to 3 molar equivalents of an amine of general formula

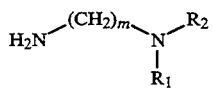  IV at a temperature of between 15° C. and 70° C. for a period of time between 15 minutes and 24 hours, in an organic solvent selected from linear or cyclic ethers and alcohols containing from 1 to 4 atoms of carbon.

The amides of formula II are isolated through evaporation of the solvent and purified if necessary through chromatography on columns of silica gel. The amides of formula II are made to react with from 1 to 2 molar equivalents of formaldehyde in a solvent selected from the alcohols containing from 1 to 4 atoms of carbon at a temperature of between 50° C. and the boiling temperature of the mixture of reaction for a period of time of between 30 minutes and 3 hours and then the reaction mixture is taken to a pH level of between 9 and 13 through the addition of a concentrated aqueous solution of an inorganic base, preferably sodium hydroxide, and then further heated to a temperature of between 50° C. and the boiling temperature of the reaction mixture for a period of time between 15 minutes and 3 hours. The products are recovered from the mixture of reaction through evaporation of the solvent and may be further purified through silica gel chromatography. When in the amide of formula II $R_3$ represents an atom of hydrogen, after the cyclization reaction a linear, ramified or cyclic ($C_1$–$C_{10}$)-alkyl radical or a benzyl radical can be inserted through treatment with an equivalent quantity of a corresponding halide in a polar solvent in the presence of between 1 to 4 molar equivalents of a base, preferably sodium hydride, potassium carbonate or sodium hydroxide, at a temperature between room temperature and the reflux temperature of the reaction mixture for a period of time of between 4 and 24 hours.

The derivatives of general formula I in which X represents an oxygen atom and n corresponds to 1 are synthesized through the reaction of the corresponding salicylic acids of general formula

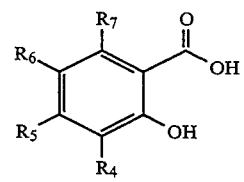

where $R_4$, $R_5$, $R_6$ and $R_7$ have the previously indicated meanings, with from 1 to 2 molar equivalents of an amine of general formula IV, in the presence of a quantity of equimolar phosphorus oxychloride with respect to the quantity of amine of general formula IV, at the boiling temperature of the reaction mixture for a period of time between 4 and 20 hours in an inert organic solvent selected from among the aromatic hydrocarbons.

The amide of general formula

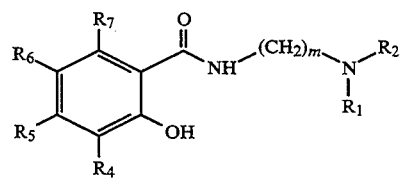

obtained in this way is then cyclized to the final product through treatment with from 1 to 2 molar equivalents of trioxane, in the presence of trifluoroacetic acid which also acts as a reaction solvent, at a temperature of between 20° C. and 70° C. for a period of time of between 8 and 24 hours.

The product of general formula I in which X represents oxygen is recovered from the reaction mixture through evaporation of the solvent, neutralization with an aqueous solution of sodium hydroxide, extraction with an organic solvent selected from among methylene chloride, chloroform and ethyl acetate and evaporation of the solvent.

The pharmacologically acceptable salts of the compounds of formula I are obtained by cold mixing equimolar quantities or in slight excess (1.1–1.2 eq.) of the suitable acid dissolved in a solvent selected from alcohols containing from 1 to 6 atoms of carbon, cyclic or acyclic ethers or their mixtures with the compounds of formula I dissolved in mixtures of the same solvents, at a temperature of between 0° C. and room temperature and filtering the precipitated salt. These salts may also be obtained by dissolving the acid, in equimolar quantities or in slight excess (1.1–1.2 eq.), and the compound of formula I in water; after evaporation of the solvent the product is crystallized by alcohols containing from 1 to 6 atoms of carbon or by their mixtures.

Salts of inorganic acids such as hydrochloric and sulphuric acids and salts of organic acids, such as oxalic, citric, tartaric, succinic and acetic acids are preferred in carrying out this invention. The salts of citric and oxalic acids are particularly preferred in performing this invention.

The melting point was determined by means of a Büchi melting point instrument, without making any corrections.

The I.R. spectrum was obtained using a Perkin-Elmer spectrophotometer mod. 281/B, usually, when not otherwise specified, preparing the sample in nujol and calibrating the spectrum between 4000 and 600 nm.

The $^1$H-NMR spectrum was calibrated at room temperature by means of a Varian Gemini spectrometer at 200 MHz, in the solvents described, using tetramethylsilane as an internal standard; the signal resonances were expressed in p.p.m.

The $^{13}$C-NMR spectrum was performed at 50.3 MHz with a Varian Gemini 200 spectrometer using tetramethylsilane as an internal standard and the solvents described in the experimental section as solvents.

The mass spectrum was calibrated using a mass spectrometer VG 7070E, at 70 eV of ionization voltage and with a voltage of acceleration of 6 Kvolt.

The silica gel chromatographies were done using silica gel 60 F254 (230-400 mesh—Merck) with the eluents described in the examples, according to the method described by Clark Still W. et al. in J. Org. Chem., 43, 2923, 1978.

The biological activity of the new derivatives described in this invention was determined by means of some typical tests, both in vitro and in vivo, commonly used on compounds featuring the antiemetic and prokinetic activity described.

In tables 5, 6, 7 and 8 the significance was determined by means of Student's test on absolute values with respect to the relative controls using 10 animals per group in tests 5, 6 and 7. The standard errors were found to be less than 10% of the average. The significant values, with significance $p < 0.05$, have been indicated with an asterisk.

In vitro tests were carried out to evaluate the effect of the compounds of formula I and some of their pharmacologically acceptable salts on physiological peristalsis, on the action of the histamine, serotonine and acetylcholine.

The action on physiological peristalsis was evaluated on an isolated rabbit jejunum preparation, according to the method reported by Magnus J. in Pfluegers Arch. Gen. Physiol. 102, 123, 1904 and described by Beretta C. in Metodiche sperimentali di fisiologia e farmacologia, Tamburini Ed., Milano, 1972.

The effect on the histamine was evaluated on a preparation of guinea-pig ileum according to the method described by the above-mentioned authors.

The effect on the serotonine was evaluated on the fornix of the stomach of a rat according to the method of Vane J. R. in Br. J. Pharmacol. Cheroother. 12, 344, 1957.

Finally the effect on the acetylcholine was evaluated on the ascending colon of a rat, according to the method of Gaddum J. H. and Horton E. W. reported in Br. J. Pharmacol. Chemother. 14, 117, 1959.

For the evaluation of the physiological peristalsis and the action on the histamine, the rabbit jejunum and the guinea-pig ileum were removed from the animals sacrificed after 24 hours fasting, washed with Tyrode fluid at 37° C. and perfused with the same oxygenated fluid (95% oxygen and 5% carbon dioxide) at the temperature of 37° C. The rabbit jejunum was used to evaluate the extent of the spontaneous peristaltic contractions in the presence and in the absence of the derivatives being studied.

The effect on the spontaneous peristalsis was found to be greater than that of cisapride, especially as regards the compounds in examples 1 and 2, although with greater concentrations than the reference, and with identical concentrations for the compound in example 6, as shown in Table 1 below. These results in themselves suggest prokinetic activity in vivo of these products.

TABLE 1

| | Spontaneous peristaltic activity on rabbit jejunum | | |
|---|---|---|---|
| example | maximum effect % (max. increase of extent of the contractions) | concentration required to obtain the maximum effect | $CE_{50}$ (concentration able to produce 50% of the maximum effect) |
| 1 | +75.0 | $1 \times 10^{-5}$M | $3 \times 10^{-6}$M |
| 2 | +73.0 | $1 \times 10^{-5}$M | $3 \times 10^{-7}$M |
| 3 | +25.0 | $1 \times 10^{-6}$M | $1 \times 10^{-8}$M |
| 4 | +11.1 | $3 \times 10^{-5}$M | $3 \times 10^{-6}$M |
| 5 | +21.7 | $3 \times 10^{-5}$M | $3 \times 10^{-6}$M |
| 6 | +50.0 | $3 \times 10^{-8}$M | $1 \times 10^{-8}$M |
| 7 | +45.5 | $1 \times 10^{-5}$M | $6 \times 10^{-6}$M |
| 8 | +12.0 | $2 \times 10^{-5}$M | $3 \times 10^{-6}$M |
| cisapride | +40.0 | $3 \times 10^{-8}$M | $2 \times 10^{-8}$M |

On the guinea-pig ileum the cumulative dose-response curve to histamine were recorded in the presence of increasing concentrations of the products being examined.

The experimental results, shown in Table 2, highlight how the compounds demonstrate antagonist activity only at very high concentrations, without causing any sensitization of the reactive towards the histamine, except in the compound in example 8.

TABLE 2

| | Influence on the activity of histamine on guinea-pig ileum | |
|---|---|---|
| example | effect | active concentration |
| 1 | non competitive antagonism | $1 \times 10^{-4}$M |
| 2 | non competitive antagonism | $1 \times 10^{-4}$M |
| 3 | mixed antagonism | $1 \times 10^{-6}$M–$1 \times 10^{-4}$M |
| 4 | competitive antagonism | $1 \times 10^{-5}$M–$1 \times 10^{-4}$M |
| 5 | competitive antagonism | $1 \times 10^{-4}$M |
| 6 | non competitive antagonism | $1 \times 10^{-5}$M |
| 7 | competitive antagonism | $1 \times 10^{-6}$M–$1 \times 10^{-4}$M |
| 8 | increase/ sensitization | $1 \times 10^{-6}$M–$1 \times 10^{-5}$M |
| cisapride | very slight sensitization at low doses | $1 \times 10^{-8}$M–$1 \times 10^{-7}$M |

Although they do not demonstrate and cannot predict any prokinetic activity, these last figures make it reasonable to presume that the compounds described have no sedative action involving the central nervous system (mediated by the $H_1$ receptors) to the pharmacologically active concentrations on the physiological peristalsis.

The effect of the products on the contracturing action of the acetylcholine was studied on the isolated ascending colon of rat, taken from Wistar rat sacrificed after 24 hours fasting, washed with De Jalon fluid at 27° C. and perfused with the same oxygenated fluid (95% oxygen and 5% carbon dioxide) at the temperature of 27° C. In this case too the cumulative dose-response curves were recorded in the presence of increasing concentrations of the products being studied.

Table 3 below shows how the compounds described in this invention antagonize the acetylcholine at concentrations which are generally higher than the reference cisapride.

TABLE 3

| example | Influence on the acetylcholine activity on the rat ascending colon | |
|---|---|---|
| | effect | active concentration |
| 1 | non competitive antagonism | $1 \times 10^{-4}M$ |
| 2 | non competitive antagonism | $1 \times 10^{-4}M$ |
| 3 | mixed antagonism | $1 \times 10^{-5}M - 1 \times 10^{-4}M$ |
| 4 | non competitive antagonism | $1 \times 10^{-5}M - 1 \times 10^{-4}M$ |
| 5 | mixed antagonism | $1 \times 10^{-6}M - 1 \times 10^{-4}M$ |
| 6 | non competitive antagonism | $1 \times 10^{-6}M - 1 \times 10^{-5}M$ |
| 7 | non competitive antagonism | $1 \times 10^{-4}M$ |
| 8 | competitive antagonism | $1 \times 10^{-4}M$ |
| cisapride | non competitive antagonism | $1 \times 10^{-6}M$ |

The absence of antagonizing properties towards a mediator involved in physiological peristalsis, at the concentrations which are otherwise active on spontaneous motility, see table 1, may further support a prokinetic action of the compounds. The figures also show that the compounds described have no atropine-like effects: this may thus suggest that there are no atropine-like effects in vivo involving the central nervous system, at the active concentrations on peristalsis.

The action on the serotonine was evaluated on the fornix of the stomach of rat, also taken from Wistar rat sacrificed after 24 hours fasting, following the technique reported by Vane J. R. in Br. J. Pharmacol. Chemoter. 12, 344, 1957, as previously described.

The results shown in Table 4 below demonstrate that the compounds of the examples 1, 2, 5, 6 and 7 increase the effect of the serotonine while the compounds of examples 3, 4 and 8 act as competitive antagonists but all at higher concentrations than the reference cisapride.

TABLE 4

| example | Influence on the serotonine activity on the fornix of the rat stomach | |
|---|---|---|
| | effect | active concentration |
| 1 | increase/ sensitization | $1 \times 10^{-5}M$ |
| 2 | increase/ sensitization | $1 \times 10^{-5}M$ |
| 3 | competitive antagonism | $1 \times 10^{-5}M - 1 \times 10^{-4}M$ |
| 4 | competitive antagonism | $1 \times 10^{-6}M - 1 \times 10^{-4}M$ |
| 5 | increase/ sensitization | $1 \times 10^{-5}M - 1 \times 10^{-4}M$ |

TABLE 4-continued

| example | Influence on the serotonine activity on the fornix of the rat stomach | |
|---|---|---|
| | effect | active concentration |
| 6 | increase/ sensitization | $1 \times 10^{-6}M - 1 \times 10^{-5}M$ |
| 7 | increase/ sensitization | $1 \times 10^{-5}M - 1 \times 10^{-4}M$ |
| 8 | competitive antagonism | $1 \times 10^{-5}M - 1 \times 10^{-4}M$ |
| cisapride | competitive antagonism | $1 \times 10^{-7}M - 1 \times 10^{-6}M$ |

The compounds described interfere with the serotonine only at higher concentrations than those active on the physiological peristalsis and therefore, at these concentrations, they do not interfere in a negative sense on the serotoninergic transmission. The reference cisapride was used in the tests described above, as a control, after being dissolved in tamtic acid at 0.75% at the concentration of 0.15% (w/v).

The prokinetic action was evaluated in vivo on Swiss albino mice determining the influence of the products on the intestinal transit of an opaque meal, according to the method described by Macht D. I. and Barba-Gose J. in J. Amer. Pharm. Ass. 20, 558, 1931 and later by Witkin L. B. et al. in J. Pharmacol. Exp. Ther. 133, 400, 1961, modified in that the measure of the tract passed through by the opaque meal was calculated as starting from the cardias rather than from the pylonas.

The method involved the administration of an opaque meal to the mice after a 24 hour fast, through gastric probe, 15 minutes after the administration of the product.

After sacrificing the animals 20 minutes after the administration of the opaque meal, the percentage of the length of the intestine travelled by the opaque meal was calculated. The experimental data, shown in tables 5 and 6, highlight a good variation in percentage with respect to the controls, often higher than the prokinetic activity of eisapride, taken as the reference drug.

TABLE 5

| example | treatment/ ($\mu$g/Kg p.o., 15' before the opaque meal) | % of intestine (from pylorus to anus) travelled by the opaque meal | variation in % with respect to the controls |
|---|---|---|---|
| 1 | 9.8 (DE$_{50}$) | 52.0 | 34.4* |
| 2 | 26.5 (DE$_{50}$) | 38.9 | 0.5 |
| 3 | 9.8 | 45.0 | 11.1 |
| 4 | 26.5 | 41.0 | 1.2 |
| 5 | 9.8 | 49.0 | 11.4 |
| 6 | 3.7 | 47.8 | 19.0 |
| 7 | 5.8 (DE$_{50}$) | 49.0 | 2.6 |
| 8 | 5.8 | 44.3 | 0.7 |
| cisapride | 19.0 (DE$_{50}$) | 43.6 | 6.0 |

TABLE 6

Test of the progression of the opaque meal in the mouse evaluated at a dose five times greater than ED$_{50}$

| Example | % of intestine (from pylorus to anus) travelled by the opaque meal | Variation % with respect to the controls |
|---|---|---|
| 1 | 54.3 | 33.7* |
| 3 | 43.2 | 6.4 |
| 4 | 48.8 | 20.2* |
| 5 | 48.0 | 18.2 |
| 8 | 53.4 | 31.5* |
| cisapride | 41.5 | 2.2 |

In particular, the prokinetic activity evaluated at a dose 5 times greater than $ED_{50}$, shown in table 6, demonstrates that the compounds according to the invention are considerably more active than the reference drug, especially considering that they generally carry out these activities at considerably lower doses than cisapride.

Within the gastro-duodenal tract, the prokinetic activity was evaluated by means of the test of gastric dumping in the rat, according to the method reported by Scarpignato C. in J. Pharmacol. 14, 261, 1983. The figures shown in table 7 below for the products of examples 1 and 6 indicate a high level of activity on the gastric dumping, especially for the compound in example 6 in comparison with cisapride.

TABLE 7

Test of gastric dumping in the rat

| Example | Treatment (30' before the administration of the coloured meal) | Increase % of the gastric dumping with respect to the controls 20' after the coloured meal |
|---|---|---|
| 1 | 12.5 μg/kg | 27.6 |
|   | 25.0 μg/kg | 70.2* |
|   | 50.0 μg/kg | 81.0* |
|   | 100.0 μg/kg | 40.0* |
|   | 200.0 μg/kg | 45.7* |
|   | 400.0 μg/kg | 34.0* |
| 6 | 3.0 μg/kg | 55.0* |
|   | 6.0 μg/kg | 72.0* |
|   | 12.5 μg/kg | 100.3* |
|   | 25.0 μg/kg | 109.2* |
|   | 50.0 μg/kg | 160.0* |
|   | 75.0 μg/kg | 161.5* |
| cisapride | 10.0 μg/kg | 23.3 |
|   | 50.0 μg/kg | 1.6 |
|   | 100.0 μg/kg | 23.3 |
|   | 300.0 μg/kg | 39.0* |

Finally the antiemetic activity was evaluated in the pigeon after induction of emesis with cisplatin, according to the method of Preziosi P. et al. in Eur. J. Pharmacol. 221, 343, 1992. The animals were subjected to treatment with the compounds of the examples 1 and 6 and with cisapride one hour before treatment with 7.5 mg/kg of cisplatin to induce vomit and the observation was continued for 3 hours after treatment with cisplatin.

The figures shown in table 8 below highlight a good antiemetic activity of the products evaluated, especially as regards the compound of example 6 in the dose of 100 mcg/kg.

The acute toxicity ($LD_{50}$) of the derivatives described in this invention was evaluated according to the method reported by Lietchfield J. T. and Wilcoxon F. in J. Pharmacol. Exp. Ther. 96, 99, 1949, on Sprague-Dawley rats of both sexes, over an observation period of 14 days from the day of treatment.

The results shown in table 9 below demonstrate that the compounds considered have a lower toxicity than cisapride.

TABLE 9

Study of acute toxicity

| example | $LD_{50}$ (mg/Kg/i.v.) |
|---|---|
| 1 | 100 |
| 2 | 75–80 |
| 6 | 45 |
| 7 | 150 |
| 10 | 83 |
| 11 | 80 |
| 12 | 130 |
| 13 | 40 |
| cisapride | 35 |

The biological results obtained in the experiments performed in vitro and in vivo demonstrate the high prokinetic and antiemetic activity of the derivatives described in this invention in comparison with cisapride, as well as their positive effect on the action of the mediators acetylcholine, serotonine and histamine.

Finally, preliminary studies on the effects as regards behaviour have been performed by means of Irwin's test, according to the method reported by Irwin S. in Gordon Res. Conf. on Medicinal Chem. 1959, 133, 1959, modified in that rats were used instead of mice. After administration by i.p. of 20 mg/Kg of the compounds of the examples 1, 3, 5 and 6 no significant variations with respect to the controls were observed in the parameters regarding consciousness, mood, motor activity, excitation of the central nervous system, posture, lack of motor coordination, muscular tone, reflexes and autonomous nervous system.

The examples reported below must be considered as an illustration of this invention and not as a limitation of it.

EXAMPLE 1

6-Chloro-3-[2-(diethylamino)ethyl]-2,3-dihydro-4(1H)-quinazolinone oxalate a) Synthesis of 2-amino-5-chloro-N-[2-(diethylamino)ethyl]benzamide 22.00 Grammes (111 mmoles) of 5-chloroisatoic anhydride are suspended in 100 ml of dioxane and at room temperature, 23.40 ml (170 mmoles) of N,N-diethylaminoethylamine are added in drops, after which the temperature is kept at 60° C. for 15 minutes.

The raw solid is recovered through evaporation of the solvent, dissolved again in methylene chloride and

TABLE 8

Test of vomit from cisplatin in the pigeon

| Example | Treatment (i.m.) Dose (μg/kg) | N° Anim | Animals that vomit % | Acts of vomit (average/anim.) | Latency of 1st act of vomit | Variation % of the time of latency with respect to the controls |
|---|---|---|---|---|---|---|
| Physiol. |  | 16 | 87.5 | 12.3 | 84.5 min. |  |
| 1 | 50.0 | 4 | 100.0 | 5.0* | 77.5 min. | −8.3 |
|   | 100.0 | 4 | 100.0 | 4.0* | 97.0 min. | +14.7 |
| 6 | 50.0 | 6 | 100.0 | 3.0* | 131 min.* | +55.0 |
|   | 100.0 | 6 | 0.0* | 0.0* |  |  |
|   | 500.0 | 6 | 33.0* | 2.3* | 105 min. | +24.3 |
| cisapride | 50.0 | 6 | 66.0 | 3.0* | 165.0 min.* | +95.5 |
|   | 100.0 | 6 | 66.0 | 2.5* | 150.0 min.* | +77.5 | washed with an aqueous solution of sodium hydroxide at pH 8.

Once recovered through evaporation of the solvent, the product is chromatographed on silica gel columns with the eluent chloroform-isopropanolammonia 30:20:1. After evaporation of the elution solvent an oily substance is obtained, with a yield of 76%, with the following chemical-physical characteristics:

$^1$H-NMR (CDCl$_3$) ppm: 1.02 (6H, t); 2.55 (6H, q+t); 3.41 (2H, q); 5.57 (1H, broad); 6.57 (1H, d); 7.09 (1H, dd); 7.31 (1H, d)

I.R. (film)cm$^{-1}$: 3350, 2990, 1650, 1580, 1530, 1330, 1260, 830, 780 b) Synthesis of 6-chloro-3-[2-(diethylamino)ethyl]-2,3-dihydro-4(1H)-quinazolinone 21.60 Grammes (80.0 mmoles) of 2-amino-5-chloro-N-[2-(diethylamino)ethyl]benzamide and 6.0 ml (80.0 mmoles) of formaldehyde in aqueous solution at 40% (w/v) are dissolved in 130 ml of ethyl alcohol and the solution is heated up to reflux for 60 minutes.

After the addition of 65 ml of an aqueous solution at 80% (w/v) of sodium hydroxide, the reaction is heated to 100° C. for 20 minutes and the raw product is obtained through evaporation of the solvent.

The solid is dissolved in ethyl acetate and washed with an aqueous solution of sodium hydroxide at pH 8.4; the product is recovered through evaporation of the solvent and subsequent purification through silica gel chromatography with eluent of chloroform-isopropanol-ammonia 30:20:1. After evaporation of the elution solvent the product desired is obtained, with a yield of 80%, with the following chemical-physical characteristics:

m.p.=60° C.

$^1$H-NMR (CDCl$_3$) ppm: 1.00 (6H, t); 2.55 (4H, q); 2.66 (2H, t); 3.55 (2H, t); 4.36 (1H, broad); 4.69 (2H, d); 6.61 (1H, d); 7.20 (1H, dd); 7.86 (1H, d)

I.R. (nujol) cm$^{-1}$: 3300, 1635, 1465, 1380, 1330, 825, 780 c) Synthesis of 6-chloro-3-[2-(diethylamino)ethyl]-2,3-dihydro-4(1H)-quinazolinone oxalate 16.90 Grammes (60.0 mmoles) of 6-chloro-3-[2-(diethylamino)ethyl]-2,3-dihydro-4(1H)-quinazolinone are dissolved in 25 ml of ethyl alcohol, to which, at the temperature of 4° C., 170 ml of a solution containing 8.32 grammes (66.0 mmoles) of dihydrate oxalic acid in a mixture of ethyl ether-ethyl alcohol in the ratio 5:1 are added.

The product immediately crystallizes and is recovered through filtration with a yield of 81%. It presents the following chemical-physical characteristics:

m.p.=130° C.

$^1$H-NMR (D$_2$O)ppm: 1.20 (6H, t); 3.10–3.40 (6H, q+t); 3.76 (2H, t); 4.54 (2H, s); 6.73 (1H, d); 7.26 (1H, dd); 7.55 (1H, d)

$^{13}$C-NMR (DMSO)ppm: 8.4 (CH$_3$); 39.5 (N—CH$_2$—CH$_2$); 46.5 (N—CH$_2$—CH$_3$); 47.4 (N—CH$_2$—CH$_2$); 58.8 (N—CH$_2$—N); 116.7 (C arom.); 116.9 (CH arom.); 121.4 (C arom.); 127.1 (CH arom.); 133.3 (CH arom.); 148.2 (C arom.); 162.9 (N—C=O); 164.6 (O—C=O)

IR (nujol) cm$^{-1}$: 3300, 1750, 1640, 1470, 1390, 1200, 840, 720

Elementary analysis:
calculated C 51.73 H 5.97 N 11.32 O 21.55 Cl 9.42
found C 50.85 H 5.91 N 11.42 O 21.61 Cl 9.59

EXAMPLE 2

6-Chloro-3-[2-(diethylamino)ethyl]-2,3-dihydro-1-methyl-4(1H)-quinazolinone oxalate a) Synthesis of 6-chloro-3-[2-(diethylamino)ethyl]-2,3-dihydro-1-methyl-4(1H)-quinazolinone 4.11 Grammes (14.6 mmoles) of 6-chloro-3-[2-(diethylamino)ethyl]-2,3-dihydro-4(1H)-quinazolinone are dissolved in 40 ml of anhydrous dimethylacetamide, to which 1.05 grammes (43.8 mmoles) of sodium hydride at 60% previously washed with pentane are added.

After 30 minutes 1.00 ml (16.1 mmoles) of methyl iodide are slowly added in drops.

The reaction mixture is diluted with water after 5 hours and the product is extracted with ether; the product is recovered through evaporation of the solvent and purified through silica gel chromatography with eluent of chloroform-methanol-water 25:25:1. After evaporation of the elution solvent an oily substance is obtained, with a yield of 81%, with the following chemical-physical characteristics:

$^1$H-NMR (CDCl$_3$) ppm: 1.01 (6H, t); 2.05 (3H, s); 2.37–2.75 (6H, t+q); 3.55 (2H, t); 4.52 (2H, s); 6.61 (1H, d); 7.25 (1H, dd); 7.86 (1H, d)

b) Synthesis of 6-chloro-3-[2-(diethylamino)ethyl]-2,3-dihydro-1-methyl-4(1H)-quinazolinone oxalate 3.25 Grammes (11.0 mmoles) of 6-chloro-3-[2-(diethylamino)ethyl]-2,3-dihydro-1-methyl-4(1H)-quinazolinone in 5 ml of ethyl alcohol are added, at the temperature of 4° C., by 30 ml of a solution containing 1.52 grammes (12.1 mmoles) of dihydrate oxalic acid in a mixture of ethyl ether-ethyl alcohol in a ratio of 5:1.

The product immediately crystallizes and is recovered through filtration with a yield of 72%. It presents the following chemical-physical characteristics:

M+=296 (loss of oxalate ion)
m.p.=156° C.

$^1$H-NMR (D$_2$O) ppm: 1.30 (6H, t); 2.78 (3H, s); 3.15–3.45 (6H, t+q); 3.82 (2H, t); 4.45 (2H, s); 6.70 (1H, d); 7.32 (1H, dd); 7.53 (1H, d)

$^{13}$C-NMR (D$_2$O) ppm: 10.8 (CH$_3$); 37.8 (N—CH$_3$); 43.5 (N—CH$_2$—CH$_2$); 50.7 (N—CH$_2$—CH$_3$); 51.9 (N—CH$_2$—CH$_2$); 68.9 (N—CH$_2$—N); 117.7 (CH arom.); 119.8 (C arom.); 126.6 (C arom.); 130.4 (CH arom.); 137.4 (CH arom.); 151.4 (C arom.); 168.1 (N—C=O); 168.8 (O—C=O)

IR (nujol) cm$^{-1}$: 1650, 1610, 1500, 1465, 1380, 1260, 1220, 820, 710

Elementary analysis:
calculated C 52.97 H 6.28 N 10.91 O 20.77 Cl 9.08
found C 51.58 H 6.15 N 10.70 O 20.84 Cl 8.99

EXAMPLE 3

6-Chloro-3-3-(diethylamino)propyl-2,3-dihydro-4(1H)-quinazolinone oxalate a) Synthesis of 2-amino-5-chloro-N-[3-(diethylamino)propyl]benzamide A solution containing 4.00 grammes (20.3 mmoles) of 5-chloroisatoic anhydride in 25 ml of dioxane at room temperature is joined by 4.80 ml (30.4 mmoles) of 3-diethylamino-1-propylamine.

The reaction is kept at room temperature for 60 minutes; the product is then obtained through evaporation of the organic solvent and purification through silica gel chromatography with eluent chloroform-isopropanol-ammonia 30:20: 1. After evaporating the elution solvent, an oily substance is obtained, with a yield of 80%, with the following chemical-physical characteristics:

$^1$H-NMR (CDCl$_3$) ppm: 0.99 (6H, t); 1.67 (2H, m); 2.47–2.60 (6H, q+t); 3.42 (2H, m); 5.75 (2H, broad); 6.54 (1H, d); 7.03 (1H, dd); 7.27 (1H, d); 8.96 (1H, broad)

b) Synthesis of 6-chloro-3-[3-(diethylamino)propyl]-2,3-dihydro-4(1H)-quinazolinone A solution containing 3.86 grammes (13.0 mmoles) of 2-amino-5-chloro-N-[3(diethylamino)propyl]benzamide in 30 ml of ethanol is joined by 1.00 ml (13.0 mmoles) of an aqueous solution of formaldehyde at 40% (w/v) and the reaction mixture is heated up to reflux for 2 hours.

The solution is joined by 10 ml of an aqueous solution at 80% (w/v) of sodium hydroxide and the temperature is kept at 100° C. for 20 minutes; the raw product is recovered through evaporation of the solvent, dissolved in ethyl acetate and washed with an aqueous solution of sodium hydroxide with pH 11.

The solid which is obtained through evaporation of the organic solvent is purified through silica gel chromatography with eluent chloroform-isopropanolammonia 35:15:1. After evaporating the elution solvent an oily substance is obtained, with a yield of 70%, with the following chemical-physical characteristics:

$^1$H-NMR (CDCl$_3$) ppm: 0.91 (6H, t); 1.67 (2H, m); 2.30–2.50 (6H, m); 3.40 (2H, t); 4.52 (2H, s); 4.74 (1H, broad); 6.55 (1H, d); 7.10 (1H, dd); 7.75 (1H, d)

c) Synthesis of 6-chloro-3-[3-(diethylamino)propyl]-2,3-dihydro-4(1H)-quinazolinone oxalate 2.38 Grammes (8.0 mmoles) of 6-chloro-3-[3-(diethylamino)propyl]-2,3-dihydro-4(1H)-quinazolinone dissolved in 4 ml of ethyl alcohol are joined, at the temperature of 4° C., by a solution containing 1.11 grammes (8.8 mmoles) of dihydrate oxalic acid in 10 ml of a mixture of ethyl ether-ethyl alcohol in the ratio 5:1.

The product crystallizes immediately and is recovered through filtration with a yield of 70% and has the following chemical-physical characteristics:

M$^+$=295 (loss of oxalate ion)
m.p.=125° C.

$^1$H-NMR (CD$_3$OD) ppm: 1.18 (6H, t); 1.91 (2H, m); 3.05 (6H, m); 3.45 (2H, t); 4.61 (2H, s); 6.80 (1H, d); 7.28 (1H, dd); 7.58 (1H, d)

$^{13}$C-NMR (DMSO) ppm: 8.4 (CH$_3$); 21.6 (CH$_2$); 41.9 (N—CH$_2$—CH$_2$); 46.1 (N—CH$_2$—CH$_3$); 48.3 (N—CH$_2$—CH$_2$); 58.6 (N—CH$_2$—N); 116.9 (CH atom.); 117.1 (C arom.); 121.4 (C arom.); 127.2 (CH atom.); 133.0 (CH arom.); 148.1 (C arom.); 162.5 (N—C=O); 165.3 (O—C=O)

IR (nujol) cm$^{-1}$: 3450, 1660, 1460, 1380, 1320, 1220, 830, 760

Elementary analysis:
calculated C 52.97 H 6.28 N 10.91 O 20.77 Cl 9.08
found C 52.72 H 6.24 N 10.78 O 20.65 Cl 9.05

EXAMPLE 4

6-Chloro-3-[3-(diethylamino)propyl]-2,3-dihydro-1-methyl-4(1H)-quinazolinone oxalate a) Synthesis of 6-chloro-3-[3-(diethylamino)propyl]-2,3-dihydro-1-methyl(1H)-quinazolinone 795 Milligrammes (33.0 mmoles) of 60% sodium hydride is added to 3.25 grammes (11.0 mmoles) of 6-chloro-3-[3-(diethylamino)propyl]-2,3-dihydro-4(1H)-quinazolinone in 30 ml of anhydrous dimethylacetamide and the solution is kept at room temperature, in an atmosphere of inert gas, for 30 minutes.

0.75 ml (12.1 mmoles) of methyl iodide are slowly added in drops and after 5 hours the reaction mixture is diluted with water and ice; the product is extracted with ethyl ether and recovered by evaporation of the organic solvent in an oily form with a yield of 90%. It has the following chemical-physical characteristics:

$^1$H-NMR (CDCl$_3$)ppm: 1.01 (6H, t); 1.79 (2H, m); 2.46–2.59 (6H, m); 2.87 (3H, s); 3.54 (2H, t); 4.43 (2H, s); 6.62 (1H, d); 7.31 (1H, dd); 7.92 (1H, d)

b) Synthesis of 6-chloro-3-[3-(diethylamino)propyl]-2,3-dihydro-1-methyl-4(1H)-quinazolinone oxalate 2.78 Grammes (9.0 mmoles) of 6-chloro-3-[3-(diethylamino)propyl]-2,3-dihydro-1-methyl-4(1H)-quinazolinone dissolved in 5 ml of ethyl alcohol are joined, at the temperature of 4° C., by 12.00 ml of a solution containing 1.25 grammes (9.9 mmoles) of dihydrate oxalic acid in a mixture of ethyl ether-ethyl alcohol in a ratio of 5:1.

The product immediately crystallizes and is recovered through filtration with a yield of 74% and shows the following chemical-physical characteristics:

M$^+$=309 (loss of oxalate ion)
m.p.=130° C.

$^1$H-NMR (DMSO) ppm: 1.15 (6H, t); 1.91 (2H, m); 2.83 (3H, s); 2.90–3.20 (6H, q+t); 3.35–3.58 (2H, m); 4.52 (2H, s); 6.85 (1H, d); 7.42 (1H, dd); 7.63 (1H, d)

$^{13}$C-NMR (DMSO) ppm: 8.4 (CH$_3$); 21.6 (CH$_2$—CH$_2$—CH$_2$); 35.3 (N—CH$_3$); 42.0 (N—CH$_2$—CH$_2$); 46.1 (N—CH$_2$—CH$_3$); 48.3 (N—CH$_2$—CH$_2$); 65.3 (N—CH$_2$—N); 114.7 (CH arom.); 118.5 (C arom.); 122.3 (C atom.); 127.4 (CH arom.); 133.3 (CH arom.); 148.7 (C arom.); 162.0 (N—C=O); 165.3 (O—C=O)

IR (nujol) cm$^{-1}$: 3450, 1740, 1670, 1610, 1500, 1460, 1380, 1220, 820, 720

Elementary analysis:
calculated C 54.11 H 6.56 N 10.52 O 20.04 Cl 8.76
found C 53.50 H 6.58 N 10.31 O 20.12 Cl 8.69

EXAMPLE 5

6-Chloro-2,3-dihydro-3-[2-(1-pyrrolidinyl)ethyl]-4(1H)-quinazolinone oxalate a) Synthesis of 2-amino-5-chloro-N-[2-(1-pyrrolidinyl)ethyl]benzamide 3.05 Milliliters (24.2 mmoles) of N-(2-aminoethyl)-pyrrolidine are dripped into a solution containing 4.00 grammes (20.2 mmoles) of 5-chloroisatoic anhydride in 40 ml of dioxane and the solution is kept for 2 hours at 60° C. and 18 hours at room temperature.

The raw solid, obtained through evaporation of the solvent, is dissolved in ethyl acetate, washed with an aqueous solution of sodium hydroxide with pH 10 and recovered through evaporation of the organic solvent with a yield of 91%. It has the following chemical-physical characteristics:

m.p.=141° C.

$^1$H-NMR (CDCl$_3$) ppm: 1.81 (4H, m); 2.57 (4H, m); 2.70 (2H, t); 3.50 (2H, m); 5.52 (2H, s); 6.61 (1H, d); 6.75 (1H, broad); 7.13 (1H, dd); 7.32 (1H, d)

b) Synthesis of 6-chloro-2,3-dihydro-3-[2-(1-pyrrolidinyl)ethyl]-4(1H)-quinazolinone 4.85 Grammes (18.1 mmoles) of 2-amino-5-chloro-N-[2-(1-pyrrolidinyl)ethyl]benzamide and 1.36 ml (18.1 mmoles) of a 40% (w/v) aqueous solution of formaldehyde are dissolved in 20 ml of ethanol and kept at reflux for 2 hours.

After the addition of 13 ml of an 80% (w/v) aqueous solution of sodium hydroxide the solution is heated to 100° C. and after 45 minutes the precipitated solid is filtered, obtaining a product, with a yield of 87%, with the following chemical-physical characteristics:

m.p. = 152° C.

¹H-NMR (CD₃OD) ppm: 1.77 (4H, m); 2.40-2.80 (6H, m); 3.62 (2H, t); 4.60 (2H, d); 6.70 (1H, d); 7.20 (1H, dd); 7.70 (1H, d)

c) Synthesis of 6-chloro-2,3-dihydro-3-[2-(1-pyrrolidinyl)ethyl]-4(1H)-quinazolinone oxalate A solution containing 2.17 grammes (17.3 mmoles) of dihydrate oxalic acid in 40 ml of water is added to 4.40 grammes (15.7 mmoles) of 6-chloro-2,3-dihydro-3-[2-(1-pyrrolidinyl)ethyl]-4(1H)-quinazolinone; the raw product is recovered through evaporation of the solvent and then crystallized by ethanol. The pure product, obtained with a yield of 34%, has the following chemical-physical characteristics:

M⁺ = 279 (loss of oxalate ion)
m.p. = 160° C.

¹H-NMR (DMSO) ppm: 1.89 (4H, m); 3.29 (6H, m); 3.70 (2H, t); 4.66 (2H, s); 6.79 (1H, d); 7.28 (1H, dd); 7.57 (1H, d)

¹³C-NMR (DMSO) ppm: 22.7 (CH₂); 41.1 (N—CH₂—CH₂); 51.3 (N—CH₂—CH₂); 53.3 (N—CH₂); 58.8 (N—CH₂—N); 116.8 (C arom.); 117.0 (CH arom.); 121.4 (C arom.); 127.2 (CH arom.); 133.2 (CH arom.); 148.2 (C arom.); 162.9 (N—C=O); 165.4 (O—C=O)

IR (nujol) cm⁻¹: 3450, 3220, 1650, 1470, 1380, 1310, 1230, 830, 710

Elementary analysis:
calculated C 52.02 H 5.46 N 11.38 O 21.67 Cl 9.47
found C 51.05 H 5.38 N 11.15 O 21.41 Cl 9.19

EXAMPLE 6

1-Benzyl-6-chloro-3-[2-(diethylamino)ethyl]-2,3-dihydro-4(1H)-quinazolinone oxalate a) Synthesis of 1-benzyl-6-chloro-3-[2-(diethylamino)ethyl]-2,3-dihydro-4(1H)-quinazolinone 3.40 Grammes (12.1 mmoles) of 6-chloro-3-[2-(diethylamino)ethyl]-2,3-dihydro-4(1H)-quinazolinone are suspended in 30 ml of a mixture of water and ethanol in a ratio of 1:1.

After the addition of 820 milligrammes (20.5 mmoles) of sodium hydroxide, 3.68 grammes (26.6 mmoles) of potassium carbonate and 3.18 ml (26.6 mmoles) of benzyl bromide, the suspension is placed in reflux for 10 hours and at room temperature for 12 hours.

The solution is concentrated and the raw product is collected with ethyl acetate and washed with an acidic aqueous solution.

The product in the pure form is obtained through silica gel chromatography with eluent chloride of methylene-isopropylic alcohol-ammonia in the ratio of 80:20:1. After evaporation of the solvent of elution an oil is obtained, with a yield of 50%, having the following chemical-physical characteristics:

¹H-NMR (CD₃COCD₃) ppm: 0.90 (6H, t); 2.30-2.70 (6H, q+t); 3.52 (2H, t); 4.55 (2H, s); 4.75 (2H, s); 6.80 (1H, d); 7.18 (1H, dd); 7.25 (5H, m); 7.80 (1H, d)

b) Synthesis of 1-benzyl-6-chloro-3-[2-(diethylamino)ethyl]-2,3-dihydro-4(1H)-quinazolinone oxalate 763 Milligrammes (6.1 mmoles) of dihydrate oxalic acid dissolved in 20 ml of a mixture of ethyl ether-ethyl alcohol in a ratio of 5:1 are added to 2.00 grammes (6.1 mmoles) of 1-benzyl-6-chloro-3-[2-(diethylamino)ethyl]-2,3-dihydro-4(1H)-quinazolinone and the product, which immediately crystallizes, is recovered through filtration with a yield of 50%. The product obtained has the following chemical-physical characteristics:

m.p. = 126° C.

¹H-NMR (CDCl₃) ppm: 1.32 (6H, t); 3.10-3.30 (6H, q+t); 3.80 (2H, t); 4.50 (2H, s); 4.67 (2H, s); 6.70 (1H, d); 7.20-7.40 (6H, m); 7.88 (1H, d)

IR (nujol) cm⁻¹: 1730, 1650, 1580, 1420, 1265, 1020, 855, 800

Elementary analysis:
calculated C 59.80 H 6.11 N 9.10 O 17.32 Cl 7.67
found C 59.63 H 6.23 N 9.18 O 17.85 Cl 7.34

EXAMPLE 7

6-Chloro-3-[2-(diethylamino)ethyl]-2,3-dihydro-4H-1,3-benzoxazin-4-one oxalate a) Synthesis of 5-chloro-[2-(diethylamino)ethyl]-salicylamide chlorohydrate 7.70 Grammes (44.7 mmoles) of 5-chlorosalicylic acid and 8.20 grammes (16.4 mmoles) of N,N-diethylaminoethylphosphoramide trichlorhydrate are dissolved in 90 ml of xylene and heated up to reflux for 20 hours. The excess solvent is separated from the oily product and the product is washed with water with neutral pH. The product is then crystallized by isopropylic alcohol and is obtained with a yield of 60%. It has the following chemical-physical characteristics:

M⁺ = 270 (loss of oxalate ion)
m.p. = 132° C.

¹H-NMR (DMSO) ppm: 1.25 (6H, t); 3.00-3.40 (6H, m); 3.55-3.85 (2H, m); 7.00 (1H, d); 7.40 (1H, dd); 8.05 (1H, d); 9.30 (1H, broad)

IR (nujol) cm⁻¹: 3240, 2580, 2480, 1630, 1585, 1545, 1455, 1370, 1150, 810, 700 b) Synthesis of 6-chloro-3-[2-(diethylamino)ethyl]-2,3-dihydro-4H-1,3-benzoxazin-4-one 8.00 Grammes (26.1 mmoles) of 5-chloro-N-[2-(diethylamino)ethyl]salicylamide hydrochloride are dissolved in 100 ml of trifluoroacetic acid with 2.35 grammes (26.1 mmoles) of trioxane and left to react for 20 hours at a temperature of 50° C.

The excess organic solvent is eliminated through evaporation; the reaction mixture is neutralized with a 4N aqueous solution of sodium hydroxide and the product is extracted with chloroform and recovered from the organic phase through evaporation of the solvent.

An oily substance, with a yield of 80%, is obtained which has the following chemical-physical characteristics:

H-NMR (CD₃COCD₃) ppm: 1.00 (6H, t); 2.55 (4H, q); 2.63 (2H, t); 3.65 (2H, t); 5.40 (2H, s); 7.04 (1H, d); 7.50 (1H, dd); 7.80 (1H, d)

c) Synthesis of 6-chloro-3-[2-(diethylamino)ethyl]-2,3-dihydro-4H-1,3-benzoxazin-4-one oxalate 1.97 Grammes (15.6 mmoles) of dihydrate oxalic acid dissolved in 20 ml of water are added to 4.01 grammes (14.2 mmoles) of 6-chloro-3-[2(diethylamino)ethyl]-2,3-dihydro-4H- 1,3-benzoxazin-4-one.

The raw product is recovered through evaporation of the solvent and is then crystallized by ethyl alcohol.

The pure product is obtained with a yield of 8055 and has the following chemical-physical characteristics:

M⁺ = 282 (loss of oxalate ion)
m.p. = 142° C.

¹H-NMR (DMSO) ppm: 1.18 (6H, t); 3.00-3.30 (6H, m); 3.80 (2H, t); 5.40 (2H, s); 7.12 (1H, d); 7.58 (1H, dd); 7.72 (1H, d)

$^{13}$C-NMR (DMSO) ppm: 8.6 (CH$_3$); 39.1 (N—CH$_2$—CH$_2$); 46.5 (N—CH$_2$—CH$_3$); 48.0 (N—CH$_2$—CH$_2$); 78.3 (N—CH$_2$—O); 119.1 (CH arom.); 120.1 (C arom.); 126.8 (C arom.); 127.1 (CH arom.); 134.4 (CH arom.); 156.7 (C arom.); 161.1 (N—C=O); 165.1 (O—C=O)

(nujol) cm$^{-1}$: 1690, 1640, 1610, 1470, 1370, 1300, 1200, 840, 710

Elementary analysis:
calculated C 5 1.60 H 5.69 N 7.53 O 25.79 Cl 9.40
found C 51.53 H 5.72 N 7.35 O 26.15 Cl 9.25

EXAMPLE 8

6-Chloro-3-[3-(diethylamino)propyl]-2,3-dihydro-4H-1,3-benzoxazin-4-one oxalate a) Synthesis of 5-chloro-N-[3-(diethylamino)propyl]-salicylamide A solution containing 2.40 ml (15.2 mmoles) of 3-diethylamino-1-propylamine in 20 ml of xylene is joined by 0.80 ml (8.5 mmoles) of phosphoryl chloride at the temperature of 4° C.

After 30 minutes, at room temperature, 4.00 grammes (23.2 mmoles) of 5-chlorosalicylic acid are directly added to the solution.

After 4 hours in reflux the raw product is recovered from the reaction mixture through evaporation of the solvent and then purified through silica gel chromatography with eluent chloroform-methanol-ammonia 30:20:1. After evaporation of the elution solvent an oily substance is obtained with a yield of 30%.

b) Synthesis of 6-chloro-3-[3-(diethylamino)propyl]-2,3-dihydro-4H-1,3-benzoxazin-4-one 1.70 Grammes (6.0 mmoles) of 5-chloro-N-[3-(diethylamino)propyl]salicylamide and 540 milligrammes (6.0 mmoles) of trioxane are dissolved in 30 ml of trifluoroacetic acid and the reaction mixture is kept at room temperature for 16 hours.

The raw product, recovered through evaporation of the solvent, is then neutralized in an aqueous solution 4N of sodium hydroxide, extracted with ethyl acetate and recovered from the organic phase through evaporation of the solvent. An oily substance is obtained with a yield of 83%.

c) Synthesis of 6-chloro-3-[3-(diethylamino)propyl]-2,3-dihydro-4H-1,3-benzoxazin-4-one oxalate 555 Milligrammes (4.4 mmoles) of dihydrate oxalic acid dissolved in 15 ml of water are added to 1.18 grammes (4.0 mmoles) of 6-chloro-3-[3-(diethylamino)propyl]-2,3-dihydro-4H- 1,3-benzoxazin-4-one and the raw product, recovered through evaporation of the solvent, is crystallized by ethyl alcohol.

The pure product is obtained with a yield of 75% and has the following chemical-physical characteristics:

M$^+$=296 (loss of oxalate ion)
m.p.=174° C.
$^1$H-NMR (DMSO) ppm: 1.12 (6H, t); 1.90 (2H, broad); 3.05 (6H, m); 3.52 (2H, t); 5.38 (2H, s); 7.12 (1H, d); 7.55 (1H, dd); 7.75 (1H, d)
$^{13}$C-NMR (DMSO) ppm: 8.4 (CH$_3$); 22.3 (CH$_2$—CH$_2$—CH$_2$); 41.4 (N—CH$_2$—CH$_2$); 46.1 (N—CH$_2$—CH$_3$); 48.3 (N—CH$_2$—CH$_2$); 78.1 (N—CH$_2$—O); 119.0 (CH arom.); 120.3 (C arom.); 126.8 (C arom.); 127.1 (CH arom.); 134.2 (CH arom.); 156.7 (C arom.); 160.8 (N—C=O); 165.1 (O—C=O)
IR (nujol) cm$^{-1}$: 1670, 1460, 1360, 1020, 830
Elementary analysis:
calculated C 52.83 H 6.00 N 7.25 O 24.85 Cl 9.06
found C 51.63 H 5.90 N 7.10 O 24.42 Cl 8.85

EXAMPLE 9

6-Chloro-2,3-dihydro-1-methyl-3-[2-(1-pyrrolidinyl)ethyl]-4(1H)-quinazolinone oxalate a) Synthesis of 6-chloro-2,3-dihydro-1-methyl-3-[2-(1-pyrrolidinyl)ethyl]-4(1H)-quinazolinone 543 Milligrammes (22.5 mmoles) of 60% sodium hydride are added to 3.50 grammes (12.5 mmoles) of 6-chloro-2,3-dihydro-3-[2-(pyrrolidino)ethyl]-4(1H)-quinazolinone in 25 ml of anhydrous dimethylacetamide and the solution is left at room temperature, in agitation and in an inert gas atmosphere, for 30 minutes. 0.86 Ml (13.8 mmoles) of methyl iodide are slowly dripped and the reaction mixture is kept for 6 hours at room temperature. The reaction mixture is then diluted with water and ice and the product is extracted with ethyl ether and recovered through evaporation of the organic solvent, obtaining an oily substance, with a yield of 14%, presenting the following chemical-physical characteristics:

$^1$H-NMR (CD$_3$COCD$_3$) ppm: 1.72 (4H, m); 2.40–2.80 (6H, m); 2.92 (3H, s); 3.65 (2H, t); 4.61 (2H, s); 6.80 (1H, d); 7.38 (1H, dd); 7.78 (1H, d)

b) Synthesis of 6-chloro-2,3-dihydro- 1-methyl-3-[2-(1-pyrrolidinyl)ethyl]-4(1H)-quinazolinone oxalate 189 Milligrammes (1.5 mmoles) of dihydrate oxalic acid dissolved in 28 ml of a mixture consisting of ethyl ether and ethyl alcohol in a ratio of 5:1 are added to 400 milligrammes (1.4 mmoles) of 6-chloro-2,3-dihydro-1-methyl-3-[2-(pyrrolidino)ethyl]-4(1H)-quinazolinone in 5 ml of ethyl alcohol at the temperature of 4° C.

The product which crystallizes immediately is recovered through filtration with a yield of 80% and presents the following chemical-physical characteristics:

M$^+$=293 (loss of oxalate ion)
$^1$H-NMR (D$_2$O) ppm: 2.10 (4H, m); 2.83 (3H, s); 2.99–3.35 (2H, m); 3.40–4.00 (6H, m); 4.82 (2H, s); 6.72 (1H, d); 7.36 (1H, dd); 7.59 (1H, d)

EXAMPLES 10–14

Salts with Citric acid

General method 7.0 Mmoles of derivative of formula I, in the form of free base, are dissolved in 5 ml of ethyl alcohol and, while in agitation and, at the temperature of 4° C., are joined by 20 ml of a solution containing 7.7 mmoles of citric acid in a mixture consisting of ethyl ether and ethyl alcohol in a ratio of 5:1.

The product, which crystallizes directly from the reaction mixture, is recovered by filtration and recrystallized if necessary in a suitable solvent.

EXAMPLE 10

6-Chloro-3-[2-(diethylamino)ethyl]-2,3-dihydro-4(1H)-quinazolinone citrate

The product obtained, according to the general method, with a yield of 93%, presents the following chemical-physical characteristics:

m.p.=161° C.
$^1$H-NMR (DMSO) ppm: 1.00 (6H, t); 2.30–2.50 (4H, m); 2.75–3.05 (6H, m); 3.52 (2H, t); 4.50 (2H, s); 6.65 (1H, d); 6.87 (1H, s); 7.18 (1H, dd); 7.42 (1H, d)
$^{13}$C-NMR (DMSO) ppm: 9.5 (CH$_3$); 40.6 (N—CH$_2$—CH$_2$); 44.0 (N—CH$_2$—CH$_3$); 46.7 (CO—CH$_2$—C—); 48.6 (N—CH$_2$—CH$_2$); 58.8 (N—CH$_2$—N); 71.5 (C—OH); 116.6 (CH arom.); 121.1 (C arom.); 126.8

(CH arom.); 132.9 (CH arom.); 147.8 (C arom.); 162.4 (C arom.); 171.3 (O—C=O); 176.4 (N—C=O); 197.3 (O—C—C(O)=O)

IR (nujol) cm$^{-1}$: 3300, 1730, 1640, 1630, 1590, 1460, 1380, 1220, 810, 660

Elementary analysis:
calculated C 50.72 H 5.96 N 8.88 O 27.04 Cl 7.39
found C 50.08 H 5.96 N 8.58 O 26.55 Cl 7.24

EXAMPLE 11

6-Chloro-3-[2-(diethylamino)ethyl]-2,3-dihydro-1-methyl-4(1H)-quinazolinone citrate The product obtained, according to the general method, with a yield of 70%, presents the following chemical-physical characteristics:

m.p.=145° C.

$^1$H-NMR (D$_2$O) ppm: 1.23 (6H, t); 2.71 (4H, q); 2.75 (3H, s); 3.24 (4H, q); 3.34 (2H, t); 3.77 (2H, t); 4.45 (2H, s); 6.71 (1H, d); 7.33 (1H, dd); 7.55 (1H, d)

$^{13}$C-NMR (D$_2$O) ppm: 10.8 (CH$_3$); 37.9 (N—CH$_3$); 43.5 (N—CH$_2$—CH$_2$); 46.4 (N—CH$_2$—CH$_3$); 50.8 (CO—CH$_2$—C—); 51.9 (N—CH$_2$—CH$_2$); 68.9 (N—CH$_2$—N); 76.5 (C—OH); 117.8 (CH arom.); 119.9 (C arom.); 126.7 (C arom.); 130.4 (CH arom.); 137.4 (CH arom.); 151.5 (C arom.); 168.2 (N—C=O); 177.7 (O—C=O); 181.5 (O—C—C(O)=O)

IR (nujol) cm$^{-1}$: 1720, 1640, 1590, 1400, 1250, 1240, 1010, 850, 790

EXAMPLE 12

6-Chloro-3-[2-(diethylamino)ethyl]-2,3-dihydro-4H-1,3-benzoxazin-4-one citrate

The product obtained, according to the general method, with a yield of 90%, presents the following chemical-physical characteristics:

m.p.=160° C.

$^1$H-NMR (DMSO) ppm: 1.10 (6H, t); 2.55 (4H, q); 2.95 (4H, q); 3.05 (2H, t); 3.70 (2H, t); 5.37 (2H, s); 7.17 (1H, d); 7.60 (1H, dd); 7.75 (1H, d)

$^{13}$C-NMR (DMSO) ppm: 9.4 (CH$_3$); 40.0 (N—CH$_2$—CH$_2$); 43.9 (N—CH$_2$—CH$_3$); 46.6 (CO—CH$_2$—C—); 48.9 (N—CH$_2$—CH$_2$); 71.8 (C—OH); 78.4 (O—CH$_2$—N); 119.0 (CH arom.); 120.2 (C arom.); 125.8 (C arom.); 127.1 (CH arom.); 134.4 (CH arom.); 155.7 (C arom.); 161.7 (N—C=O); 171.9 (O—C=O); 176.8 (O—C—C(O)=O)

IR (nujol) cm$^{-1}$: 1740, 1680, 1640, 1590, 1470, 1380, 1220, 820, 770

EXAMPLE 13

1-Benzyl-6-chloro-3-12-(diethylamino)ethyl]-2,3-dihydro-4(1H)-quinazolinone citrate The product obtained, according to the general method, with a yield of 77%, presents the following chemical-physical characteristics:

m.p.=112° C.

$^1$H-NMR (DMSO) ppm: 1.12 (6H, t); 2.50 (1H, s); 2.60 (4H, dd); 3.00 (6H, t+q); 3.66 (2H, t); 4.60 (2H, s); 4.78 (2H, s); 5.95 (3H, broad); 6.83 (1H, d); 7.31 (5H, s); 7.35 (1H, dd); 7.68 (1H, d)

$^{13}$C-NMR (DMSO) ppm: 9.5 (CH$_3$); 40.7 (N—CH$_2$—CH$_2$); 44.1 (N—CH$_2$—CH$_3$); 47.0 (CO—CH$_2$—C); 48.7 (N—CH$_2$—N); 52.4 (N—CH$_2$—CH$_2$); 64.4 (N—CH$_2$—Ph); 72.0 (C—OH); 115.5 (CH arom.); 118.3 (C arom.); 122.1 (C arom.); 127.5 (CH arom.); 127.6 (CH arom.); 127.7 (CH arom.); 128.9 (CH arom.); 133.3 (CH arom.); 137.2 (C arom.); 147.3 (C arom.); 162.4 (N—C=O); 171.7 (O—C=O); 176.6 (O—C—C(O)=O).

IR (nujol) cm$^{-1}$: 1730, 1650, 1580, 1490, 1450, 1380, 1360, 1260, 1220, 1180, 820, 750.

Elementary analysis:
calculated C 57.50 H 6.08 N 7.45 O 22.69 Cl 6.29
found C 57.38 H 5.95 N 7.35 O 22.80 Cl 6.40

EXAMPLE 14

6-Chloro-1-cyclohexylmethyl-3-[2-(diethylamino)ethyl]-2,3-dihydro-4(1H)-quinazolinone citrate a) Synthesis of 6-chloro-1-cyclohexylmethyl-3-[2-(diethylamino)ethyl]-2,3-dihydro-4(1H)-quinazolinone 2.00 Grammes (7.1 mmoles) of 6-chloro-3-[2-(diethylamino)ethyl]-2,3-dihydro-(1H)-quinazolinone are suspended in 5 ml of anhydrous dimethylacetamide. Milligrammes (17.8 mmoles) of sodium hydride are added to this solution and, after 30 minutes at room temperature, 0.72 ml (7.8 mmoles) of bromomethylcyclohexane are dripped. After 3 hours of reaction at room temperature the reaction solution is poured into water and ice. The product, of an oily consistency, is recovered through extraction with ethyl acetate, with a yield of 85%, and presents the following chemical-physical characteristics.

$^1$H-NMR (CD$_3$COCD$_3$)ppm: 1.00 (6H, t); 1.00-1.40 (6H, m); 1.50-1.95 (5H, m); 2.55 (4H, q); 2.63 (2H, t); 3.12 (2H, d); 3.53 (2H, t); 4.70 (2H, s); 6.84 (1H, d); 7.31 (1H, dd); 7.78 (1H, d)

b) Synthesis of 6-chloro-1-cyclohexylmethyl-3-[2-(diethylamino)ethyl]-2,3-dihydro-4(1H)-quinazolinone citrate 1.00 Gramme (2.7 mmoles) of 6-chloro-1-cyclohexylmethyl-3-[2(diethylamino)ethyl]-2,3-dihydro-4(1H)-quinazolinone, dissolved in 10 ml of ethyl alcohol is joined, in agitation and at the temperature of 4° C., by 10 ml of a solution of ethyl ether and ethyl alcohol in a ratio of 5:1 containing 668 milligrammes (3.2 mmoles) of monohydrate citric acid.

The product crystallizes immediately and is recovered by filtration with a yield of 70%. It presents the following chemical-physical characteristics:

m.p.=122° C.

$^1$H-NMR (DMSO) ppm: 1.12 (11H, broad); 1.65 (4H, broad); 2.58 (4H, s); 2.75-3.30 (8H, m); 3.68 (2H, t); 4.65 (2H, s); 6.88 (1H, d) 7.35 (1H, ad) 7.75 (1H, d); 8.92 (3H, broad)

$^{13}$C-NMR (DMSO) ppm: 9.4 (CH$_3$); 25.6 (CH$_2$); 26.2 (CH$_2$); 30.6 (CH$_2$); 36.4 (—CH—CH$_2$—); 40.5 (—N—CH$_2$—CH$_2$—); 44.2 (CO—CH$_2$—C); 46.8 (—N—CH$_2$—CH$_3$); 48.6 (N—CH$_2$—CH$_2$); 55.0 (—N—CH$_2$—N—); 64.5 (—N—CH$_2$); 72.0 (C—OH); 114.9 (CH arom.); 117.6 (C arom.); 121.2 (C arom.); 127.6 (CH arom.); 133.3 (CH arom.); 147.7 (C arom.); 162.6 (N—C=O); 171.8 (O—C=O); 177.5 (O—C—C(O)=O).

IR (nujol) cm$^{-1}$: 1730, 1650, 1600, 1415, 1270, 1110, 1030, 860, 800.

Elementary analysis:
calculated C 56.89 H 7.07 N 7.37 O 22.45 Cl 6.22
found C 55.95 H 7.35 N 7.50 O 22.30 Cl 6.20

EXAMPLE 15

6-Chloro-2,3-dihydro-3-[2-(4-morpholinyl)ethyl]-4(1H)-quinazolinone citrate a) Synthesis of 2-amino-5-chloro—N-[2-(4-morpholinyl)ethyl]benzamide 4.40 Milliliters (33 mmoles) of N-(2-aminoethyl)morpholine are dripped, at room temperature, into a suspension containing 6.0 g (30 mmoles) of 5chloroisatoic anhydride in 30 ml of dioxane and then the temperature is kept at 60° C. for 120 minutes.

The raw solid, obtained through evaporation of the solvent, is dissolved in ethyl acetate and washed with an aqueous solution of sodium hydroxide with pH 8.0. The desired product is recovered with a yield of 90% through evaporation of the solvent and has the following chemical-physical characteristics:

m.p.=106° C.

$^1$H-NMR (CD$_3$COCD$_3$) ppm: 2.34–2.68 (6H, m); 3.30–3.70 (6H, m); 6.25 (2H, broad); 6.76 (1H, d); 7.12 (1H, dd); 7.42 (1H, d); 7.68 (1H, broad)

I.R. (nujol) cm$^{-1}$: 3410, 3300, 1610, 1570, 1520, 1450, 1370, 1290, 1250, 1130, 1110, 900, 850 b) Synthesis of 6-chloro-2,3-dihydro-3-[2-(4-morpholinyl)ethyl]-4(1H)-quinazolinone 6.96 Grammes (25.0 mmoles) of 2-amino-5-chloro—N-[2-(4morpholinyl)ethyl]benzamide and 1.9 ml (25.0 mmoles) of a 40% (w/v) aqueous solution of formaldehyde are dissolved in 40 ml of ethyl alcohol and the solution is kept at reflux for 120 minutes.

After the addition of 18 ml of an 80% (w/v) aqueous solution of sodium hydroxide the solution is heated to 100° C. for 30 minutes and the raw product is obtained through evaporation of the solvent. The solid is dissolved in ethyl acetate and washed with an aqueous solution of sodium hydroxide with pH 8.4. The desired product is obtained with a yield of 90% through evaporation of the solvent and has the following chemical-physical characteristics:

m.p.=82° C.

$^1$H-NMR (CD$_3$COCD$_3$) ppm: 2.30–2.69 (6H, m); 3.40–3.73 (6H, m); 4.78 (2H, s); 6.18 (1H, broad); 6.80 (1H, d); 7.25 (1H, dd); 7.73 (1H, d)

I.R. (nujol) cm$^{-1}$: 3280, 1620, 1450, 1370, 1310, 1250, 1100, 900, 850 c) Synthesis of 6-chloro-2,3-dihydro-3-[2-(4-morpholinyl)ethyl]-4(1H)-quinazolinone citrate 20 Milliliters of a solution containing 1.32 g (6.30 mmoles) of monohydrate citric acid in a mixture of ethyl ether—ethyl alcohol in a ratio of 5:1 are added, at a temperature of 4° C., to a solution containing 1.70 g (5.70 mmoles) of 6-chloro-2,3-dihydro-3-[2-(4-morpholinyl)ethyl]-4(1H)-quinazolinone in 20 ml of ethyl alcohol.

The product crystallizes immediately and is recovered through filtration with a yield of 80%. It shows the following chemical-physical characteristics:

$^1$H-NMR (DMSO) ppm: 2.49–2.90 (6H, m); 2.69 (4H, dd); 3.60–3.78 (6H, m); 4.64 (2H, s); 6.79 (1H, d); 7.30 (1H, dd); 7.58 (1H, d)

$^{13}$C-NMR (DMSO) ppm: 41.1 (N—CH$_2$—CH$_2$); 43.4 (CO—CH$_2$—C—); 52.8 (O—CH$_2$—CH$_2$); 55.1 (N—CH$_2$—CH$_2$); 59.1 (N—CH$_2$—N); 65.4 (O—CH$_2$—CH$_2$); 72.5 (C—OH); 116.8 (CH arom.); 117.5 (C arom.); 121.4 (C arom.); 127.1 (CH arom.); 133.0 (CH arom.); 148.0 (C arom.); 162.5 (N—C=O); 171.7 (O—C=O); 175.5 (O—C—C(O)=O)

I.R. (nujol) cm$^{-1}$: 3300, 1720, 1630, 1450, 1375, 1190, 890, 810

Elementary analysis:
calculated C 49.27 H 5.38 N 8.62 O 29.55 Cl 7.18
found C 48.90 H 5.24 N 9.01 O 29.95 Cl 6.90

EXAMPLE 16

1-Benzyl-6-chloro-2,3-dihydro-3-[2-(4-morpholinyl)ethyl]-4(1H)-quinazolinone citrate a) Synthesis of 1-benzyl-6-chloro-2,3-dihydro-3-[2-(4-morpholinyl)ethyl]-4(1H)-quinazolinone 3.50 Grammes (11.8 mmoles) of 6-chloro-2,3-dihydro-3-[2-(4morpholinyl)ethyl]-4(1H)-quinazolinone are dissolved in 20 ml of a mixture of toluene and dimethylsulfoxide in a ratio 5:1. The solution is dripped into a suspension containing 340 mg (14.2 mmoles) of 95% sodium hydride in 30 ml of dimethylsulfoxide and the reaction mixture is kept at 40° C. for 30 minutes. Afterwards a mixture containing 2.11 ml (17.7 mmoles) of benzylbromide and 60 ml of toluene is dripped into the solution and the suspension is kept at 40° C. for 4 hours.

The raw product is extracted with ethyl acetate after dilution of the reaction mixture with water. The desired product is obtained with a yield of 40% after evaporation of the solvent and washing of the solid with cold ethyl alcohol and has the following chemical-physical characteristics:

m.p.=125° C.

$^1$H-NMR (CDCl$_3$) ppm: 2.35–2.58 (6H, m); 3.43–3.70 (6H, m); 4.39 (2H, s); 4.49 (2H, s); 6.63 (1H, d); 7.13–7.40 (6H, m); 7.89 (1H, d)

b) Synthesis of 1-benzyl-6-chloro- 2,3-dihydro-3-[2-(4-morpholinyl)ethyl]-4(1H)-quinazolinone citrate 10 Milliliters of a solution containing 0.91 g (4.20 mmoles) of monohydrate citric acid in a mixture of ethyl ether - ethyl alcohol in a ratio 5:1 are added, at the temperature of 4° C., to a solution containing 1.50 g (3.90 mmoles) of 1-benzyl-6-chloro-2,3-dihydro-3-[2-(4-morpholinyl)ethyl]-4(1H)-quinazolinone in 5 ml of ethyl alcohol.

The product immediately crystallizes and is recovered through filtration with a yield of 90%. It shows the following chemical-physical characteristics:

$^1$H-NMR (CDCl$_3$)ppm: 2.61 (4H, dd); 2.42–3.00 (6H, m); 3.62 (6H, m); 4.52 (2H, s); 4.69 (2H, s); 6.79 (1H, d); 7.20–7.38 (6H, m); 7.64 (1H, d)

$^{13}$C-NMR(DMSO) ppm: 41.2 (N—CH$_2$—CH$_2$); 43.2 (CO—CH$_2$—C—); 52.1 (N—CH$_2$—N); 53.0 (O—CH$_2$—CH$_2$); 55.6 (N—CH$_2$—CH$_2$); 64.4 (N—CH$_2$—Ph); 65.8 (O—CH$_2$—CH$_2$); 72.4 (C—OH); 115.1 (CH arom.); 118.5 (C arom.); 121.9 (C arom.); 127.3 (CH arom.); 127.4 (CH arom.); 127.5 (CH arom.); 128.7 (CH arom.); 132.8 (CH arom.); 137.2 (C arom.); 147.1 (C arom.); 161.6 (N—C=O); 171.5 (O—C=O); 175.3 (O—C—C(O)=O)

Elementary analysis:
calculated C 56.13 H 5.59 N 7.28 O 24.94 Cl 6.06
found C 56.02 H 5.31 N 7.35 O 24.92 Cl 6.40

We claim:

1. A heterocyclic compound with prokinetic and antiemetic activity of formula and a pharmacologically acceptable salt thereof wherein X is an atom of nitrogen, R$_3$ is an atom of hydrogen or a branched, linear or cyclic $(C_1-C_{10})$-alkyl or a benzyl radical, $R_1$ and $R_2$, independently, are a $(C_1-C_3)$-alkyl radical or an atom of hydrogen or taken together with the atom of nitrogen form a heterocyclic ring, m is a whole number between 2 and 3, $R_6$ is halogen, $R_4$, $R_5$ and $R_7$ are independently an atom of H or a $C_1-C_6$ alkyl.

2. The compound according to claim 1 wherein the halogen is chlorine.

3. The compound according to claim 2 which is 6-chloro-3-[2-(diethylamino)ethyl]-2,3-dihydro-4(1H)-quinazolinone and the oxalate and citrate salt thereof.

4. The compound according to claim 2 which is 6-chloro-3-[2-(diethylamino)ethyl]-2,3-dihydro-1-methyl-4(1H)-quinazolinone, the oxalate and citrate salt thereof.

5. The compound according to claim 2 which is 6-chloro-3-[3-(diethylamino)propyl]-2,3-dihydro-4(1H)-quinazolinone, and the oxalate salt thereof.

6. The compound according to claim 2 which is 6-chloro-3-[3-(diethylamino)propyl]-2,3-dihydro-1-methyl-4(1H)-quinazolinone and the oxalate salt thereof.

7. The compound according to claim 2 which is 6-chloro-2,3-dihydro-3-[2-(1-pyrrolidinyl)ethyl]-4(1H)-quinazolinone and the oxalate salt thereof.

8. The compound according to claim 2 which is 1-benzyl-6-chloro-3-[2-(diethylamino)ethyl]-2,3-dihydro-4(1H)-quinazolinone, the oxalate and citrate salt thereof.

9. The compound according to claim 2 which is 6-chloro-2,3-dihydro-1-methyl-3-[2-(1-pyrrolidinyl)ethyl]-4(1H)-quinazolinone and the oxalate salt thereof.

10. The compound according to claim 2 which is 6-chloro-1-cyclohexylmethyl-3-[2-(diethylamino)ethyl]-2,3-dihydro-4(1H)-quinazolinone and the citrate salt thereof.

11. The compound according to claim 2 which is 6-chloro-2,3-dihydro-3-[2-(4-morpholinyl)ethyl]-4(1H)-quinazolinone and the citrate salt thereof.

12. The compound according to claim 2 which is 1-benzyl-6-chloro-2,3-dihydro-3-[2-(4-morpholinyl)ethyl]-4(1H)-quinazolinone and the citrate salt thereof.

* * * * *